(12) United States Patent
Herrera et al.

(10) Patent No.: US 9,023,755 B2
(45) Date of Patent: May 5, 2015

(54) SILOXANE REMOVAL FROM GASES USING LIGNITE-ENHANCED ACTIVATED CARBONS AND ADSORBENT MEDIA USED THEREFOR

(71) Applicant: Cabot Corporation, Boston, MA (US)

(72) Inventors: David Herrera, Marshall, TX (US); Patton M. Adams, Longview, TX (US)

(73) Assignee: Cabot Corporation, Boston, MA (US)

(*) Notice: Subject to any disclaimer, the term of this patent is extended or adjusted under 35 U.S.C. 154(b) by 128 days.

(21) Appl. No.: 13/803,084

(22) Filed: Mar. 14, 2013

(65) Prior Publication Data

US 2014/0171304 A1  Jun. 19, 2014

Related U.S. Application Data

(60) Provisional application No. 61/738,743, filed on Dec. 18, 2012.

(51) Int. Cl.
| | |
|---|---|
| *C01B 31/08* | (2006.01) |
| *B01D 53/72* | (2006.01) |
| *B01D 53/04* | (2006.01) |
| *B01J 20/20* | (2006.01) |
| *B01D 53/02* | (2006.01) |
| *C12M 1/00* | (2006.01) |

(52) U.S. Cl.
CPC .............. *B01D 53/04* (2013.01); *B01J 20/20* (2013.01); *B01D 53/02* (2013.01); *B01D 2253/102* (2013.01); *B01D 2253/302* (2013.01); *B01D 2258/05* (2013.10); *C12M 47/18* (2013.01)

(58) Field of Classification Search
CPC .... B01D 53/1487; B01D 53/72; C01B 31/08; C01B 31/085
USPC ............................................ 502/416; 95/141
See application file for complete search history.

(56) References Cited

U.S. PATENT DOCUMENTS

| | | | | |
|---|---|---|---|---|
| 5,292,708 A | * | 3/1994 | Karl .............................. | 502/427 |
| 5,899,187 A | | 5/1999 | Gruber et al. | |
| 6,114,280 A | * | 9/2000 | Stephens ....................... | 502/437 |
| 7,264,648 B1 | | 9/2007 | Wetzel et al. | |
| 2012/0024157 A1 | | 2/2012 | Maheshwary et al. | |

FOREIGN PATENT DOCUMENTS

| | | |
|---|---|---|
| DE | 227 946 | 10/1985 |
| EP | 1561506 | 5/2007 |
| WO | WO 94/00382 | 1/1994 |
| WO | WO 2008/024329 | 2/2008 |
| WO | WO 2012/030560 | 3/2012 |

OTHER PUBLICATIONS

Ahrer W., et al, Hydrogen Sulfide and Siloxane Removal from Biogas for its Usage in Fuel Cells, Profactor Produktionsforschungs GmbH, 1st European FC Techn. and Appl. Conference, Rome, Dec. 14-16, 2005.

Ajhar M., et al, Siloxane Removal from Landfill and Digester Gas—A Technology Overview. Bioresource Technology 101, 2010, p. 2913-2923.

Boulinguiez, B., et al, Biogas Pre-Upgrading by Adsorption of Trace Compounds onto Granular Activated Carbons and an Activated Carbon Fiber-Cloth, Water Science & Technology, 59, 2009, p. 935-944.

Dewil, R., et al, Energy Use of Biogas Hampered by the Presence of Siloxanes, Energy Conversion and Management 47, 2006, p. 1711-1722.

Doczyck, W., Reinigung von Deponiegasen, Erfahrungen mit Organischen Siliziumverbindungen—Ursachen, Historie, Neue Reinigungskonzepte Deponiegas, 2003, verlag Abfall, aktuelle, p. 175-187. (Machine translation provided).

Finocchio, E., et al, Purification of Biogas from Siloxanes by Adsorption: On the Regenerability of Activated Carbon Sorbents, Energy & Fuels, 2009, 23, p. 4156-4159.

Huppmann, R., et al, Cyclic Siloxanes in the Biological Waste Water Treatment Process—Determination, Quantification and Possibilities of Elimination, Fresenius' Journal of Analytical Chemistry, 1996, 354, p. 66-71.

Matsui, T., et al, Removal of Siloxane from Digestion Gas of Sewage Sludge, Bioresource Technology 101, 2010, p. S29-S32.

Soreanu, G., et al, Approaches Concerning Siloxane Removal from Biogas—A Review, Canadian Biosystems Engineering, vol. 53, 2011, p. 8.1-8.18.

Wheless, E., et al, Siloxanes in Landfill and Digester Gas Update. In Proc. 27th SWANA Landfill Gas Symp., San Antonio, TX, Mar. 22-25; Solid Waste Assoc. North America: Silver Springs, MD; 2004.

Montanari T. et al., "Purification of Landfill Biogases from Siloxanes by Adsorption: A Study of Silic and 13X Zeolite Adsorbents on Hexamethylcyclotrisiloxane Separation", Chemical Engineering Journal, Elsevier Sequoia, Lausanne, CH, vol. 165, No. 3, Dec. 15, 2010, pp. 859-863.

Prochazkova A. et al., "Testovani Adsorbentu Pro Odstranovani Siloxanu Z Bioplynu", Paliva, vol. 3, Jan. 14, 2011, pp. 22-27.

International Search Report and The Written Opinion of the International Searching Authority, or The Declaration of International Patent Application No. PCT/US2013/073644, mailed on Feb. 25, 2014.

\* cited by examiner

*Primary Examiner* — Stuart Hendrickson

(57) ABSTRACT

A method of removing siloxanes from a gas stream includes flowing the gas stream that carries siloxanes through an adsorbent media to remove at least part of the siloxanes from the gas stream, wherein the adsorbent media comprises lignite-based activated carbon. A spent adsorbent media is provided that contains the lignite-based activated carbon through which a gas stream containing siloxanes has been at least partially purified, and which may be regenerated.

55 Claims, 5 Drawing Sheets

SILOXANE REMOVAL FROM GASES USING LIGNITE-ENHANCED ACTIVATED CARBONS AND ADSORBENT MEDIA USED THEREFOR

CROSS REFERENCE TO RELATED APPLICATIONS

This patent application claims the benefit of U.S. Provisional Patent Application No. 61/738,743, filed Dec. 18, 2012, the entire contents of which are incorporated herein by reference.

FIELD OF THE INVENTION

The present invention relates to siloxane removal from gas streams using lignite-based activated carbons in adsorbent media. The present invention further relates to spent adsorbent media having the lignite-based activated carbon and filter beds formed thereof.

BACKGROUND OF THE INVENTION

As energy diversification intensifies, alternative sources of energy such as biogas from landfills and digesters become more attractive. Landfill (LFG) and digester gas (DG) are both excellent sources of methane. Waste handlers and municipalities are increasingly using biogas generated at sewage treatment plants and solid waste landfills as a biofuel. Biogases can be used as a fuel to run internal combustion engines or turbines that power equipment or generate electrical power. However, these biogases can be contaminated by siloxanes, reduced sulfur compounds, and a variety of volatile organic compounds (VOC's).

Siloxanes are used in the manufacture of personal hygiene, health care and industrial products. As a consequence of their widespread use, siloxanes are found in wastewater and in solid residential and industrial waste deposited in landfills. At wastewater treatment plants and landfills, low molecular weight siloxanes can volatilize into digester gas and landfill gas. Although the amount of volatized siloxanes present in such gases may be small, the siloxanes are problematic. Siloxanes are nuisance contaminants that accumulate on energy generation equipment, resulting in increased maintenance and operating costs. When the biogas is combusted to generate power (such as in gas turbines, internal combustion engines or boilers), siloxanes are converted to silicon dioxide ($SiO_2$), which can deposit in the combustion and/or exhaust stages of the equipment. The silica deposits can cause abrasive wear on engine parts and lead to reduced engine life. The deposits also can inhibit conduction and lubrication, and also can dislodge and clog lines, or contaminate engine oil. The siloxanes in biogases thus can significantly increase wear and other damage in equipment. Manufacturers of gas turbines and reciprocating engines are increasingly calling for the reduction of the presence of siloxanes in combustion gases in order to warranty their products. Waste digesters or landfills for which the biogas is used as fuel before making any emissions have a need to remove siloxanes and other materials that may deposit on the burners. Electrical power generators that use emission catalysts with combustion of biogases that contain siloxanes also are prone to incur silica film development with consequent reductions in catalytic activity, and also have siloxane removal needs.

Landfills that vent gases directly to the atmosphere can have emission control needs that go beyond siloxane removal. Landfill gases that will be vented to the atmosphere may need to be scrubbed before release to remove not only siloxanes, but also reduced sulfur compounds (e.g., $H_2S$) and VOCs, and other contaminants that may be carried in the gas.

Sorbent media such as silica gel, layered beds, or bituminous coal and coconut activated carbon have been proposed for siloxane removal. Conventional siloxane removal strategies for biogas purification have tended to rely on multi-stage and/or multi-layer procedures including hydrogen sulfide ($H_2S$) pre-treatment followed by treatment with adsorbent media for siloxane removal. In U.S. Pat. No. 7,264,648, filter beds formed of a plurality of different layers of different filter media are described therein as being useful for siloxane removal. Bituminous coal and coconut based activated carbon, for example, are widely used in the industry for removal of many types of contaminants. Silica gel behaves like a molecular sieve, and may only perform well when targeting a single contaminant under controlled conditions. Silica gel also can have low macro-porosity which can restrict diffusion, and silica gel may be vulnerable to contaminant spikes or composition variations. "Super Siloxane Adsorbent Silica gel" by ADCOA has been marketed for use in siloxane removal.

New strategies for siloxane removal from gas streams are needed, which can provide high adsorbent capacity for siloxanes without relying on designs that are complicated and/or costly. Also, new strategies are needed for single stage or single layer removal of siloxanes and different companion contaminants from the same gas streams.

SUMMARY OF THE INVENTION

A feature of the present invention is a method for the removal of siloxanes from contaminated gas streams using lignite-based activated carbon in adsorbent media.

A further feature of the present invention is a method for the removal of siloxanes from contaminated gas streams using single bed layer comprised of lignite-based activated carbon alone or blended with one or more different sorbent media.

Another feature of the present invention is a method using adsorbent media comprising lignite-based activated carbon having a pore size distribution which can remove siloxanes at a high adsorbent capacity from contaminated gas streams for which gas flow is directed through the media or flows through the media.

An additional feature of the present invention is a method using adsorbent media comprising a blend of lignite-based activated carbon and at least one different adsorbent media which can remove siloxanes at a high adsorbent capacity and at least one other volatized or gas-borne component from the same gas stream for which gas flow is directed through the media.

A further feature of the present invention is spent adsorbent media comprising the lignite-based activated carbon through which a gas stream containing siloxane has been at least partially purified, which may be regeneratable at least in part.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages and in accordance with the purposes of the present invention, as embodied and broadly described herein, the present invention relates, in part, to a method of removing siloxanes from a contaminated gas stream, comprising flowing the gas stream comprising siloxanes through an adsorbent media to remove at least part of the siloxanes from the gas stream, wherein the adsorbent media comprises lignite-based activated carbon.

The present invention also relates to a spent adsorbent media comprising lignite-based activated carbon through which a gas stream containing siloxanes has been at least partially purified.

The present invention also relates to a filter bed comprising the spent lignite-based activated carbon.

The present invention also relates to an adsorbent media comprising lignite-based activated carbon and having siloxanes adsorbed or attached therein.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

Figure 1:
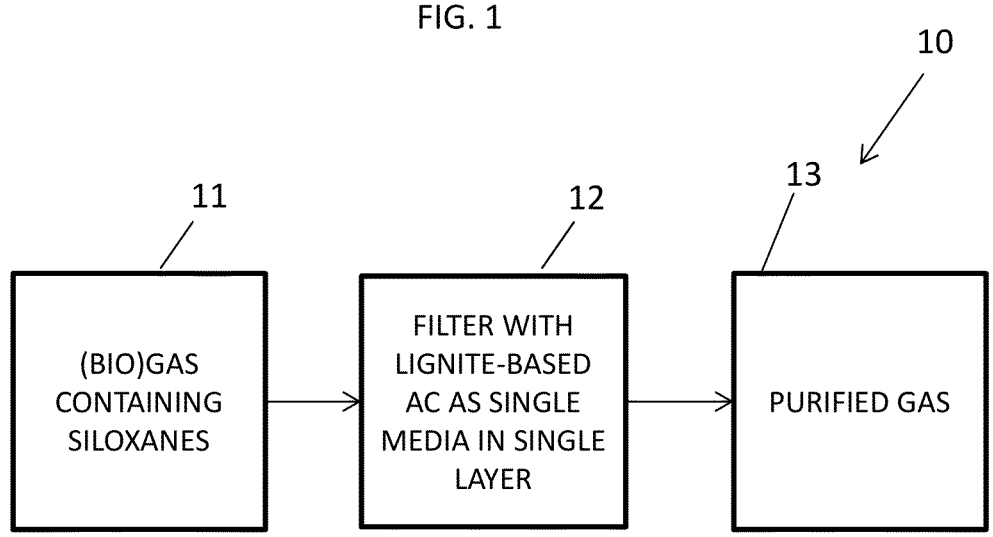
FIG. 1 shows a flow chart of a process for siloxane removal according to an example of the present application.

Siloxane removal from gas streams is provided with adsorbent media comprising lignite-based activated carbon adsorbent media. The adsorbent media can comprise lignite-based activated carbon adsorbent as a sole type of media used or in blends with different kinds of media. These sorbents can be used for biogas purification or purification of other gas streams which can carry siloxanes and, if present, other gas-borne contaminants. The lignite-based activated carbon adsorbent media can be used for removal of siloxane as the sole targeted contaminant or for concurrent removal of a combination of contaminants or "catch-all" media that includes siloxane. The lignite-based activated carbon, whether used alone or in blends in media, can be used in a single layer to achieve filtering objectives that include siloxane removal, although its use in combination with other layers is not excluded. For biogas purification, the lignite-based activated carbon can cover a spectrum of contaminants to improve siloxane removal, eliminate or support $H_2S$ pre-treatment, and/or manage VOC treatment objectives, or provide other purification effects. These sorbent media can achieve unexpectedly advantageous performance in removal of siloxane in particular, and also volatile organic compound (VOC), and total reduced sulfur compounds if needed or desired.

Treatment goals in landfill and digester gas purification may vary but siloxane removal needs are usually or often common to both applications. Due to possible high concentrations of hydrogen sulfide ($H_2S$) and VOC's, competitive adsorption can inhibit siloxane removal. As indicated, the industry has used multi-layered or gradient beds inter alia as a type of media for biogas treatment. The lignite-based activated carbons of the present application can provide high siloxane removal capacity with minimal competitive influences from other contaminants without requiring layered or gradient bed configurations.

As shown by performance data herein for tests conducted at multiple landfill and digester sites, the lignite-based activated carbon adsorbent media of this application has excellent sulfur removal performance. The test results show, for example, that both sorbents based on lignite activated carbon itself and as a blend with other sorbent media in single layer configurations can achieve up to 100 wt. % removal for siloxanes, greater than 90 wt. % removal of VOC's, and up to 100 wt. % removal of total reduced sulfur (TRS). The test results of a field test performed at a digester described herein have shown a 200% increase in engine oil life from 1,000 hours to 3,000 hours, greater than 25% increase in spark plug life, and improved siloxane removal efficiency. The test results of another field test performed at a landfill described herein demonstrate significant improvements in media longevity for the lignite-based activated carbon over a traditional (non-lignite) coal activated carbon media. These results show that use of the lignite-based activated carbon can highly effectively remove siloxanes and other contaminants present in biogas. These test results further indicate that the lignite-based activated carbon media can provide a single-media solution without need of impregnant or multi-layering of diverse media in the bed or pre-filtering, although these additional features optionally may be included.

The media comprised of lignite-based activated carbon unblended with other media can provide a high degree of meso-porosity and minimal competitive adsorption with VOC's. The test results also show that the blends of lignite activated carbon unblended with other media, such as different activated carbon, can have the ability to perform as a "catch-all" carbon. Both types of sorbents having the lignite-based activated carbon can be naturally catalytic, and can remove hydrogen sulfide with trace oxygen and moisture present.

As indicated, the lignite-based activated carbon can be used to remove siloxanes, and, optionally reduce sulfur compounds and/or VOCs from biogas. Digester operators may be, but not necessarily, concerned primarily or only about siloxane removal, and in some cases also hydrogen sulfide. Landfill operators where gases are directly vented may need removal of siloxanes, $H_2S$, and VOC's. $H_2S$ may be removed via pre-treatment. In that instance, the media beds may be mainly used for siloxanes and VOC's. The removal of reduced sulfur compounds (primarily $H_2S$) can be desirable, especially at landfills, if no such separate pre-treatment for hydrogen sulfide or total reduced sulfur (TRS) is applied. TRS can refer to the sulfur compounds which can include hydrogen sulfide, methyl mercaptan, dimethylsulfide, and dimethyldisulfide. $H_2S$ can lead to the generation of $SO_2$ and $SO_3$ during a combustion process and poses the potential for acidic/corrosive condensation in general. The removal of VOC's also may be needed or desired. The three aforementioned families of contaminants (i.e., siloxanes, reduced sulfur, VOCs) each adsorb or chemsorb differently. Activated carbon layers have frequently been characterized by carbon tetrachloride activity (CTC activity). CTC activity is a measure of micro-porosity most suitable for low molecular weight organics (i.e. VOC's) and does not adequately assess the functionality of meso-porosity or catalytic potential. The broad spectrum of contaminants that can be removed with the lignite-based activated carbon of the present application can range, for example, to compounds in the molecular weight (MW) (g/mol) range of from about 34 to about 400 or more, or from about 34 to about 300, or from about 40 to about 200, or other values. CTC activity focuses on microporosity which is limited up to 20 Å. A majority of siloxanes can be greater than 20 Å in size and have average MW's greater than 300.

Treatable biogas can be produced in many different ways, e.g., domestic waste (landfill), anaerobic waste digester (sewage) treatment, animal manure (e.g., animal feedlots), decaying vegetation compost, or any other decomposition process that generates methane, and the like. As indicated, siloxanes are present in many sources of biogas. The lignite-based activated carbon can be deployed as a cost effective method for the purification of biogas is the application of activated carbon (AC) upstream of an energy generation process (e.g., internal combustion engine, reciprocating engine, gas turbine, microturbine, boiler, catalysts, etc.). Siloxanes can be removed from biogas with the lignite-based activated carbon without disrupting the methane content such that resulting cleaned biogas can be used in combustion equipment with reduced risk of engine fouling or other damage from siloxanes. The lignite-based activated carbon can effectively eliminate siloxanes from biogas, for example, to sharply reduce or completely prevent opportunity for development and accumulation of silica deposits from siloxanes on energy generation equipment. The type of gas stream that can be treated with the lignite-based activated carbon adsorbent media to remove siloxanes is not limited to biogas. The gas streams containing siloxanes that can be treated with the lignite-based activated also can include, for example, industrial process gas streams, conditioned or ventilation air streams, or other types of gas streams containing siloxanes. The lignite-based activated carbon also can be used to filter gas streams associated with other environments, such as oxidation catalyst beds used in electrical power generation, siloxane-contaminated gas streams in semiconductor chip device manufacture, or other situations that can encounter or generate siloxane-contaminated gas streams.

The adsorption of the media comprising lignite-based activated carbon can be dominant, for example, for certain molecules, such as siloxanes, in meso-sized pores of 20-500 Å in diameter, or have other pore sizes. According to IUPAC notation, "microporous" materials have pore diameters of less than 2 nm and "macroporous" materials have pore diameters of greater than 50 nm; the mesoporous category can lie in the middle, i.e., a "mesoporous" material can be a material containing pores with diameters between 2 and 50 nm (20 Å to 500 Å). The lignite-based activated carbon can have, for example, pore sizes, wherein at least about 25%, or from about 25% to 40%, or from about 30% to about 40%, or other amounts, based on total pore volume, are from pore sizes of from 20 Å to 500 Å, and wherein total pore volume is determined based on mL/g carbon material. The mesoporosity of the lignite-based activated carbon can be indicated by a molasses decolorizing efficiency of at least 50, or at least 55, or at least 60, or at least 65, or at least 70, or at least 75, or at least 80, or at least 85, or at least 90, or at least 95, or from 50 to 100, or from 50 to 90, or other values. Molasses DE (Decolorizing Efficiency) is a measure of a carbon's ability to remove color from a standard molasses solution. The test carbon performance can be compared to a standard at 90% color removal. Coconut based activated carbon has almost zero molasses DE, and bituminous coal based activated carbon may be 30-40.

The lignite-based activated carbon can reduce siloxane content in gas streams to levels to below 150 ppb, or below 50 ppb, or below 1 ppb, or below detectible limits. A media bed containing the lignite-based activated carbon can entrap siloxane, and optionally also other unwanted gas contaminates, while allowing a high percentage (e.g., >99.9% by volume) of the original methane to flow out as cleaned fuel. The lignite-based activated carbon can be used in a carbon bed filter to remove siloxane, and if present hydrogen sulfide and VOCs, from a gas stream before the gas reaches a combustion engine or combustion turbine system. The lignite-based activated carbons can have enhanced porosity characteristics for the removal of siloxanes, and optionally other gas stream contaminants, such as acid gases, volatile organic compounds (VOC's), or other components, and increased total pore volume and mesoporosity. In addition, lignite can have high catalytic activity, neutralizing capacity, and/or alkalinity. Adsorbent media products based on the lignite-based activated carbon can be designed primarily for siloxane removal, or can be modified to suit a variety of treatment goals. Lignite-enhanced activated carbons include lignite activated carbon, and blends of lignite activated carbon with a different adsorbent media as part of the recipe. Although not desiring to be bound to theory, it is theorized that the siloxanes may selectively adsorb in the meso pores of activated carbon, therefore, giving lignite activated carbons an advantage over traditional (non-lignite) coal-based media because a greater fraction of the porosity in lignite-based activated carbon is meso-porosity. Traditional media can rely on micro-porosity, whereas lignite can be characterized by significant meso-porosity.

As indicated, the lignite-based activated carbons can be used alone or as blended with a different type of activated carbon. This variable can depend on the treatment goal of the end user. In treatment of biogas produced by anaerobic waste digesters, for example, focus usually is on siloxane removal and in some cases, acid gases like hydrogen sulfide. In landfill gas treatments, the gas treatment needs may vary, but may tend to focus on removal of siloxanes, hydrogen sulfide, and VOC's. In cases, hydrogen sulfide may be removed via separate pre-treatment, in which case the filter beds can be mainly for removing siloxanes and VOC's. Regenerative systems also may be used, wherein spent lignite-based activated carbon may be regenerated to recover at least part of the original siloxane and/or other contaminant(s) removal capacity.

The lignite-based activated carbon referenced herein can be activated carbon produced by steam activation of lignite coal. Lignite coal also is often referred to as brown coal. The lignite can be types such as xyloid lignite or compact lignite. Lignite can have a carbon content, for example, of approximately 25-35% by weight, a moisture content that can be, for example, as high as about 66% weight, and an ash content which can range, for example, from about 6% to about 19%, by weight of lignite.

Unwashed lignite product of an example of the present application can be highly selective to siloxanes and, if present, can pick up at least a portion of hydrogen sulfide ($H_2S$) and acid gases and volatile organics (VOCs). Unwashed coal is not washed coal. "Washed coal" refers to a process of using acid to remove ash content and neutralize the final product. Washing eliminates catalytic activity or its ability to remove acid gasses like H2S. Another sorbent product can be the unwashed lignite in a blend with other activated carbons, and which can pick up additional contaminants. The porosity in the unwashed lignite can be, for example, 20-36% of the total pore volume from pore sizes less than 20 Å, 25-34% of the total pore volume from pore sizes of from 20-500 Å, and 40-44% of the total pore volume from pore sizes greater than 500 Å, or other distributions. The porosity in the unwashed lignite can be, for example, 22-34% of the total pore volume from pore sizes less than 20 Å, 26-33% of the total pore volume from pore sizes of from 20-500 Å, and 40-44% of the total pore volume from pore sizes greater than 500 Å, or other distributions. The porosity in the unwashed lignite can be, for example, 23-33% of the total pore volume from pore sizes less than 20 Å, 27-32% of the total pore volume from pore sizes of from 20-500 Å, and 41-43% of the total pore volume from pore sizes greater than 500 Å, or other distributions. The total porosity of the media can be, for example, from about 0.9 to about 1.4 mL/g, or from about 1.0 to about 1.3 mL/g, or from about 1.1 to about 1.2 mL/g, or other values. The lignite-based activated carbon can have an apparent density of, for example, from about 0.3 to about 0.6 g/mL, or from about 0.35 to about 0.55 g/mL, or from about 0.4 to about 0.5 g/mL, or other values. The lignite-based activated carbon can have a BET surface area, for example, of at least 500 $m^2/g$, or from about 500 $m^2/g$ to about 650 $m^2/g$, or from about 525 $m^2/g$ to about 625 $m^2/g$, or from about 550 to about 600 $m^2/g$, or other values. Surface area (B.E.T.) is the total surface area of a solid calculated by the B.E.T. (Brunauer, Emmett, Teller) equation, from nitrogen adsorption or desorption data obtained under specified conditions; square meters per gram. The lignite-based activated carbon can have a pH, for example, of greater than 7, or greater than 7.5, or greater than 8, or greater than 9, or other values.

The lignite-based activated carbon can be formed by high temperature steam activation of unwashed lignite coal. Lignite-based activated carbon which is commercially available for other uses can be used or adapted for use in the methods of siloxane removal from contaminated gas streams of the present application. The lignite-based activated carbon has high loading capacity for siloxanes without impregnants or additives. The steam-activated lignite carbon optionally can be impregnated with a treating agent to enhance or broaden performance. The impregnation of the activated carbon can be done by mixing a solid or liquid chemical with the carbon substrate before, during, or after activation. The impregnant may be an acid, base, or salt. A large number of inorganic and organic compounds can be used for the impregnant. The impregnant can be, for example, magnesium oxide, sodium bicarbonate, sodium carbonate, sodium hydroxide, potassium hydroxide, potassium iodide, potassium permanganate, basic copper and zinc carbonates, copper and zinc sulfates, sodium molybdate, sodium vanadate, ammonium chloride, ammonium carbonate, silver nitrate, as well as TEDA (triethylenediamine) or tartaric acid and salts thereof, which can be used individually or in any combinations thereof for impregnating the activated carbons for use in gas filters. As an example, the lignite-based activated carbon can contain impregnant in an amount of from 0 to about 5 wt. %, or from 0 to about 1 wt. %, or from 0 to about 0.5 wt. %, or from 0 to about 0.1 wt. %, or from 0 to about 0.01 wt. %, or below detectible limits, or other values.

The lignite-based activated carbons can be made in particulate form as powders, granules, extruded pellets, briquettes, agglomerates, or other forms. Granular activated carbon has a relatively larger particle size compared to powdered activated carbon. Powdered activated carbon can be an activated carbon with particles predominantly smaller than 80 mesh in size. Extruded pellets can be a mixture of powdered activated carbon and binder, which are fused together and extruded into a cylindrical shaped activated carbon black. Briquettes can be a mixture of activated carbon powder and binder that is pressed in a form. The particulate forms of activated carbon can have a particle size, for example, of up to about 5 mm, or up to 4 mm, or from about 0.1 mm to about 4 mm, or from about 0.15 mm to about 3.75 mm, or from about 0.25 to about 3.5, or from about 0.5 mm to about 3 mm, or from about 1 mm to about 2.5 mm, or other sizes. At least about 50%, or at least about 60%, or at least about 70%, or at least about 80%, or at least about 90%, or from about 50% to 100% by weight, of the granular particles, briquettes, or extruded pellets used in a media layer or bed can have a size in the range of from about 2 mm to about 5 mm.

Adsorbent media can comprise the lignite-based activated carbon in an amount of at least about 40 wt. %, or at least about 50 wt. %, or at least about 60 wt. %, or at least about 70 wt. %, or at least about 80 wt. %, or at least about 90 wt %, or at least about 95 wt. %, or from about 50-100 wt. %, or from about 60-90 wt. %, or other amounts, of the adsorbent media. The adsorbent media can be present as a homogenous bed of the lignite-based activated carbon. The filter bed may be used in a single vessel of a process, or multiple vessels of a process such as in a train of vessels. As indicated, the adsorbent media also can comprise a blend of the lignite-based activated carbon and at least one different kind of adsorbent media. The at least one different kind of adsorbent media can be, for example, a different activated carbon such as activated carbon produced from bituminous coal, coconut shells, wood, sawdust, rice hulls, peat, petroleum residues, or any combinations thereof. The at least one different kind of activated carbon can have a pore size distribution, for example, that comprises a percentage of pore volume having pore sizes less than 2 nm that is greater, e.g., at least 3% greater, or at least 5% greater, or at least 10% greater, or at least 20% greater, or at least 30% greater, or at least 50% greater, than a percentage of pore volume in the lignite-based activated carbon that has pore sizes less than 2 nm. The blends of lignite-based activated carbon and different activated carbon can be proportioned to provide a spectrum of selectivities for different contaminants in addition to siloxanes without loss of the siloxane removal performance. The adsorbent media can comprise a blend of the lignite-based activated carbon and at least one non-carbon based adsorbent media, such as a silica gel. The total amounts of non-lignite based activated carbon that can be used in the blends can be, for example, up to about 60 wt. %, or up to about 50 wt. %, or up to about 40 wt. %, or up to about 30 wt. %, or up to about 20 wt. %, or up to about 10 wt. %, or up to about 5 wt. %, or from about 0-50 wt. %, or from about 10-40 wt. %, or other amounts, of the blend comprising lignite-based activated carbon.

The adsorbent media that comprises the lignite-based activated carbon can be deployed in a variety of restrained forms, such as packed column or bed, loaded canister, or impregnated nonwoven or woven fabrics. The impregnated fabrics can be in various forms, such as in roll, pleated, framed, or discrete filter pad forms. The fabrics can be organic and/or inorganic fiber constructions which can provide a substrate to which activated carbon can be attached by contacting the fabric with a thermosettable or hardenable impregnating resin in which the activated carbon is dispersed, and setting the resin. The adsorbent media may be used in fluidized or moving beds. The size of the filter bed can vary depending on the particular application and process conditions. For biogas treatment at a anaerobic digester, for example, the filter bed may be used in the form of a layer having a size of from about 90 cm to about 460 cm substantially uniform depth for a bed diameter of from about 30 cm to about 400 cm, or can have other dimensions. For biogas treatment at a landfill operation, for example, the filter bed may be used in the form of a layer having a size of from about 90 cm to about 460 cm substantially uniform depth for a bed diameter of from about 30 cm to about 400 cm, or can have other dimensions.

The lignite-based activated carbon or blend thereof in the media can be essentially uniform and homogeneous in composition throughout a filter bed or other configuration of use. For example, the composition of the media with respect to the amount of lignite-based activated carbon present, and any additional different sorbent co-present, each may not vary more than about ±5%, or not more than about ±4%, or not more than about ±3%, or not more than about ±2%, or not more than about ±1%, between any two locations within the filter bed layer or other configuration of use. The filter bed can be devoid of compositional gradients and the like.

The siloxanes removed by the adsorbent media can be, for example, a saturated silicon-oxygen hydride formed from atoms of carbon (C), hydrogen (H), oxygen (O), and silicon (Si), which includes at least one unit of alternating silicon and oxygen atoms (e.g., —$Si(R_2)$—O—$Si(R_2)$—), wherein each R can be a hydrogen atom or a hydrocarbon group (e.g., C1-C5 alkyl, such as methyl). The siloxanes that the lignite-based activate carbon and blends thereof can remove from gas streams can include volatile methyl siloxanes. The methyl siloxanes can be linear methylsiloxanes or methylcyclosiloxanes. These methyl siloxanes can be, for example, hexamethyldisiloxane (L2, MM), hexamethylcyclotrisiloxane (D3), octamethyltrisiloxane (L3, MDM), octamethylcyclotetrasiloxane (D4), decamethylcyclopentasiloxane (D5), decamethyltetrasiloxane (L4), dodecamethylpentasiloxane (L5), dodecamethylcyclohexasiloxane (D6), or others, or any combinations thereof. Common abbreviations used in the industry for these siloxanes are indicated here and used in the examples herein.

Figure 2:
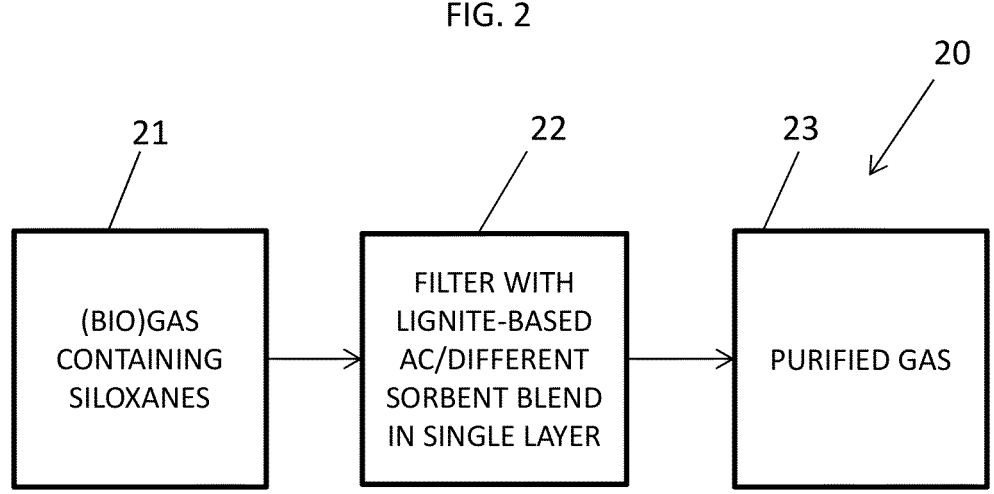
FIG. 2 shows a flow chart of a process for siloxane removal according to an example of the present application.

FIG. 1 shows a process for siloxane removal according to an example of the present application. The process 10 includes a (bio)gas stream 11 which is filtered with lignite-based activated carbon as a single media in a single layer in step 12 to provide a clean or purified gas 13. FIG. 2 shows a process 20 for siloxane removal wherein the (bio)gas 21 is filtered with a blend of lignite-based activated carbon with a different sorbent in a single layer in step 22 to provide a purified gas 23. As indicated, the gas can be a biogas or any other gas that carries volatized siloxanes.

The method of flowing the gas stream through the adsorbent media having the lignite-based activated carbon can remove siloxanes from the gas in amounts, for example, of at least about 95 wt. %, or at least about 96 wt. %, or at least about 97 wt. %, or at least about 98 wt. %, or at least about 99 wt. %, or 100 wt. % or below detectible limits, or from about 95 wt. % to 100 wt. %, or from about 96 wt. % to about 99 wt. %, or other amounts of the volatile siloxanes from the gas stream. The method can remove at least about 95 wt. % of the volatile siloxanes for a time period that is at least about 2× (i.e., two times or 100%) longer, or at least about 2.5× (i.e., 2.5 times or 150%) longer, or at least about 3× (i.e., 3 times or 200%) longer, than for adsorbent media containing an equal volume and similar bed geometry of bituminous coal-based activated carbon instead of the lignite-based activated carbon. The method can remove at least about 99 wt. % of the volatile siloxanes for a time period that is at least about 2× longer, or at least about 2.5× longer, or at least about 3× longer, than for adsorbent media containing an equal volume and similar bed geometry of bituminous coal-based activated carbon instead of the lignite-based activated carbon. These methods can be applied, for example, to treatment of a gas stream at the inlet side of the adsorbent media that contains siloxanes in amounts of from about 1 ppm to about 25 ppm, or from about 3 to about 20 ppm, or from about 5 to about 15 ppm, or other amounts of siloxanes.

As indicated, the gas stream that is treated by the method can comprise volatile siloxanes, and optionally at least one of total reduced sulfur compounds and/or volatile organic compounds, when introduced at an inlet side of the adsorbent media. The adsorbent media can remove total reduced sulfur compounds from the gas in amounts, for example, of at least about 95 wt. %, or at least about 96 wt. %, or at least about 97 wt. %, or at least about 98 wt. %, or at least about 99 wt. %, or 100 wt. % or below detectible limits, or from about 95 wt. % to 100 wt. %, or from about 96 wt. % to about 99 wt. %, or other amounts. The adsorbent media can remove VOCs from the gas in amounts, for example, of at least about 90 wt. %, or at least about 95 wt. %, or at least about 96 wt. %, or at least about 97 wt. %, or at least about 98 wt. %, or at least about 99 wt. %, or 100 wt. % or below detectible limits, or from about 90 wt. % to 100 wt. %, or from about 95 wt. % to 100 wt. %, or from about 96 wt. % to about 99 wt. %, or other amounts. The method can remove, for example, at least about 99 wt. % of the volatile siloxanes, and at least one of i) at least about 99.5 wt. % of the total reduced sulfur compounds and ii) at least about 95 wt. % of the volatile organic compounds from the gas stream. These contaminant removal rates can be provided in the treatment of a gas stream at the inlet side of the adsorbent media which contains, for example, from about 1 ppm to about 25 ppm siloxanes, from about 10 ppm to about 150 ppm total reduce sulfur compounds, and from about 200 ppm to about 500 ppm volatile organic compounds, or other compositions thereof.

The present invention also relates to a spent adsorbent media and filter beds that comprise lignite-based activated carbon through which a gas stream containing siloxanes has been at least partially purified and to which siloxanes have been adsorbed or attached. These spent adsorbent media may be regenerated at least in part for re-use. The siloxanes can present in the spent media in an amount, for example, of from about 0.1 wt % to about 60 wt %, or from about 0.2 wt % to about 60 wt %, or from about 0.3 wt. % to about 50 wt. %, or from about 0.4 wt. % to about 25 wt %, or from about 0.5 wt. % to about 10 wt. %, or other values, based on the weight of the spent adsorbent media.

The present invention includes the following aspects/embodiments/features in any order and/or in any combination:

1. A method of removing siloxanes from a gas stream, comprising flowing the gas stream comprising siloxanes through an adsorbent media to remove at least part of the siloxanes from the gas stream, wherein said adsorbent media comprises lignite-based activated carbon.

2. The method of any preceding or following embodiment/feature/aspect, wherein the lignite-based activated carbon has pore sizes and a total pore volume, wherein at least about 25% of the total pore volume is from pore sizes of from 20 Å to 500 Å.

3. The method of any preceding or following embodiment/feature/aspect, wherein the lignite-based activated carbon has pore sizes and a total pore volume, wherein from about 25% to about 40% of the total pore volume is from pores sizes of from 20 Å to 500 Å.

4. The method of any preceding or following embodiment/feature/aspect, wherein the lignite-based activated carbon having a pore size distribution of:
   about 20% to about 36% of total pore volume from pore sizes less than 20 Å,
   about 25% to about 40% of total pore volume from pore sizes of from 20 Å to 500 Å, and
   about 40% to about 44% of total pore volume from pore sizes greater than 500 Å.

5. The method of any preceding or following embodiment/feature/aspect, wherein the lignite-based activated carbon has a molasses decolorizing efficiency of at least 50.

6. The method of any preceding or following embodiment/feature/aspect, wherein the lignite-based activated carbon has an apparent density of from about 0.3 to about 0.6 g/mL.

7. The method of any preceding or following embodiment/feature/aspect, wherein the lignite-based activated carbon has a total porosity of from about 0.9 to about 2.0 mL/g.

8. The method of any preceding or following embodiment/feature/aspect, wherein the lignite-based activated carbon has a BET surface area of from about 500 to about 650 $m^2/g$.

9. The method of any preceding or following embodiment/feature/aspect, wherein the lignite-based activated carbon has a pH greater than 7.

10. The method of any preceding or following embodiment/feature/aspect, wherein the lignite-based activated carbon is in powder form or bound form.

11. The method of any preceding or following embodiment/feature/aspect, wherein the lignite-based activated carbon is in the form of granular particles, briquettes, or extruded pellets.

12. The method of any preceding or following embodiment/feature/aspect, wherein at least 50% of the granular particles, briquettes, or extruded pellets have a size in the range of from about 2 mm to about 5 mm.

13. The method of any preceding or following embodiment/feature/aspect, wherein the lignite-based activated carbon is steam-activated unwashed lignite.

14. The method of any preceding or following embodiment/feature/aspect, wherein the adsorbent media comprises at least about 50 wt. % lignite-based activated carbon.

15. The method of any preceding or following embodiment/feature/aspect, wherein the adsorbent media comprises at least about 90 wt. % lignite-based activated carbon.

16. The method of any preceding or following embodiment/feature/aspect, wherein the adsorbent media is present as a homogenous bed of the lignite-based activated carbon.

17. The method of any preceding or following embodiment/feature/aspect, wherein the adsorbent media comprises a blend of the lignite-based activated carbon and at least one different kind of adsorbent media.

18. The method of any preceding or following embodiment/feature/aspect, wherein the adsorbent media comprises a blend of the lignite-based activated carbon and at least one different kind of activated carbon.

19. The method of any preceding or following embodiment/feature/aspect, wherein the at least one different kind of activated carbon is activated carbon produced from bituminous coal, coconut shells, wood, sawdust, rice hulls, peat, petroleum residues, or any combinations thereof.

20. The method of any preceding or following embodiment/feature/aspect, wherein the at least one different kind of activated carbon has a pore size distribution comprising a percentage of pores having pore sizes less than 2 nm that is greater than a percentage of pores in the lignite-based activated carbon that has pore sizes less than 2 nm.

21. The method of any preceding or following embodiment/feature/aspect, wherein at least one of the lignite-based activated carbon and the at least one different kind of activated carbon are impregnated with at least one impregnant that is a salt, an acid, or base.

22. The method of any preceding or following embodiment/feature/aspect, wherein the adsorbent media comprises a blend of the lignite-based activated carbon and at least one non-carbon based adsorbent media.

23. The method of any preceding or following embodiment/feature/aspect, wherein the adsorbent media comprises a blend of the lignite-based activated carbon and silica gel.

24. The method of any preceding or following embodiment/feature/aspect, wherein the flowing of the gas stream through the adsorbent media removes at least about 95 wt. % of the volatile siloxanes from the gas stream.

25. The method of any preceding or following embodiment/feature/aspect, wherein the flowing of the gas through the adsorbent media removes at least about 95 wt. % of the volatile siloxanes for a time period that is at least about 2× longer than for adsorbent media containing an equal volume and same bed geometry of bituminous coal-based activated carbon instead of the lignite-based activated carbon.

26. The method of any preceding or following embodiment/feature/aspect, wherein the flowing of the gas through the adsorbent media removes at least about 95 wt. % of the volatile siloxanes for a time period that is at least about 3× longer than for adsorbent media containing an equal volume and same bed geometry of bituminous coal-based activated carbon instead of the lignite-based activated carbon.

27. The method of any preceding or following embodiment/feature/aspect, wherein the gas stream at the inlet side of the adsorbent media contains from about 1 ppm to about 25 ppm siloxanes, 28. The method of any preceding or following embodiment/feature/aspect, wherein the gas stream comprises volatile siloxanes, total reduced sulfur compounds and volatile organic compounds, when introduced at an inlet side of the adsorbent media.

29. The method of any preceding or following embodiment/feature/aspect, wherein the flowing of the gas stream through the adsorbent media removes at least about 95 wt. % of the volatile siloxanes from the gas stream.

30. The method of any preceding or following embodiment/feature/aspect, wherein the flowing of the gas stream through the adsorbent media removes at least about 95 wt. % of total reduced sulfur compounds.

31. The method of any preceding or following embodiment/feature/aspect, wherein the flowing of the gas stream through the adsorbent media removes at least about 90 wt. % of the volatile organic compounds from the gas stream.

32. The method of any preceding or following embodiment/feature/aspect, wherein the flowing of the gas stream through the adsorbent media removes at least about 99 wt. % of the volatile siloxanes from the gas stream.

33. The method of any preceding or following embodiment/feature/aspect, wherein the flowing of the gas stream through the adsorbent media removes at least about 99 wt. % of the volatile siloxanes, and at least one of i) at least about 99.5 wt. % of the total reduced sulfur compounds and ii) at least about 95 wt. % of the volatile organic compounds from the gas stream.

34. The method of any preceding or following embodiment/feature/aspect, wherein the flowing of the gas through the adsorbent media removes at least about 95 wt. % of the volatile siloxanes for a time period that is at least about 2× longer than for adsorbent media containing an equal volume and same bed geometry of bituminous coal-based activated carbon instead of the lignite-based activated carbon.

35. The method of any preceding or following embodiment/feature/aspect, wherein the flowing of the gas through the adsorbent media removes at least about 95 wt. % of the volatile siloxanes for a time period that is at least about 3× longer than for adsorbent media containing an equal volume and same bed geometry of bituminous coal-based activated carbon instead of the lignite-based activated carbon.

36. The method of any preceding or following embodiment/feature/aspect, wherein the gas stream at the inlet side of the adsorbent media contains from about 1 ppm to about 25 ppm siloxanes, from about 10 ppm to about 150 ppm total reduce sulfur compounds, and from about 200 ppm to about 500 ppm volatile organic compounds.

37. The method of any preceding or following embodiment/feature/aspect, wherein the siloxanes comprise linear siloxanes, cyclic siloxanes, or any combinations thereof.

38. The method of any preceding or following embodiment/feature/aspect, wherein the siloxanes comprise polymethylpolysiloxane, polymethylcyclopolysiloxane, or any combinations thereof.

39. The method of any preceding or following embodiment/feature/aspect, wherein the gas stream comprises landfill gas emissions.

40. The method of any preceding or following embodiment/feature/aspect, wherein the gas stream comprises gas emissions from anaerobic digestion.

41. The present invention also relates to a spent adsorbent media comprising lignite-based activated carbon through which a gas stream containing siloxanes has been at least partially purified.

42. The spent adsorbent media comprising lignite-based activated carbon of any preceding or following embodiment/feature/aspect.

43. The present invention also relates to a filter bed comprising the spent lignite-based activated carbon of any preceding or following embodiment/feature/aspect.

44. The present invention also relates to an adsorbent media comprising lignite-based activated carbon of any preceding or following embodiment/feature/aspect and having siloxanes adsorbed or attached therein.

45. The adsorbent media of any preceding or following embodiment/feature/aspect, wherein the siloxanes are present in an amount of from about 0.1 wt % to about 60 wt %, based on the weight of said adsorbent media.

46. The adsorbent media of any preceding or following embodiment/feature/aspect, wherein the siloxanes are present in an amount of from about 0.2 wt % to about 60 wt %, based on the weight of said adsorbent media.

47. The adsorbent media of any preceding or following embodiment/feature/aspect, wherein the lignite-based activated carbon has a pore size distribution of:
about 20% to about 36% of total pore volume from pore sizes less than 20 Å,
about 25% to about 40% of total pore volume from pore sizes of from 20 Å to 500 Å, and
about 40% to about 44% of total pore volume from pore sizes greater than 500 Å.

48. The adsorbent media of any preceding or following embodiment/feature/aspect, wherein said siloxanes comprises hexamethyldisiloxane, hexamethylcyclotrisiloxane, octamethyltrisiloxane, octamethylcyclotetrasiloxane, decamethylcyclopentasiloxane, decamethyltetrasiloxane, dodecamethylpentasiloxane, dodecamethylcyclohexasiloxane, or any combinations thereof.

The present invention will be further clarified by the following examples, which are intended to be only exemplary of the present invention. Unless indicated otherwise, all amounts, percentages, ratios and the like used herein are by weight.

EXAMPLES

Lignite-based activated carbon was field tested as an adsorbent sorbent at three biogas-generating locations that included a waste landfill at one site and anaerobic digesters of sewage treatment facilities at two different geographical sites.

Two different forms of lignite-based activated carbon were tested. In a first form, referred to herein as "AC1", activated carbon obtained as steam-activated unwashed lignite coal was used as the adsorbent media. AC1 had a high degree of meso-porosity. AC1 had a pore size distribution of about 20% to about 36% less than 20 Å, about 25% to about 40% from 20 Å to 500 Å, and about 40% to about 44% greater than 500 Å. "AC2" was a blend of about 50 wt. % AC1 and about 50 wt. % coconut-based activated carbon. Comparison sorbent (CS) used were non-lignite coal-based activated carbon (60 CTC activity) in 3 mm diameter pellets (CS1) or 4 mm diameter pellets (CS2), and a commercial activated carbon and graphite blend (CS3). CS1 was obtained as Norit® RB 30M and CS2 was Norit® RB 40M steam activated extruded bituminous coal and/or coconut based carbons from Norit Americas Inc., Marshall Tex., USA. CS3 was SAG™ (Selective Active Gradient) material produced by Applied Filter Technology, Evans Ga., USA.

Table 1 is an overview of the biogas studies that were performed.

TABLE 1

| Biogas Source | Sorbent Product Used | Treatment Goal | Equipment Protected | Variables Monitored |
|---|---|---|---|---|
| Digester #1 | a) AC1 b) AC2 c) CS1 or CS2 | Siloxane removal | Microturbine | VOC's, $H_2S$, siloxanes |
| Digester #2 | a) AC2 b) SAG | Siloxane removal | IC Engine | Siloxanes |
| Landfill #1 | AC2 | Siloxane removal | Oxidation Catalyst | VOC's, reduced sulfur species, siloxanes |

Example 1

In a proof of concept study performed at Digester #1, gas samples were taken from a 2-vessel (series configuration)

carbon adsorption system using TEDLAR® bags. Samples were taken from the outlet and tested for siloxane content via gas chromatography with atomic emission detection (GC-AED). Both linear (L) and cyclic (D) siloxanes were reported. Testing was performed on three media: standard media (CS1) (3 mm pellets, 60 CTC activity), AC1, and AC2. The filter bed dimensions used were 122 cm depth and 30 cm diameter. This was a dual vessel arrangement, wherein both vessels had the same size and were arranged in series. The standard operating conditions for the adsorption system in these tests are shown in Table 2.

TABLE 2

| System Operating Conditions | |
|---|---|
| Pressure (psig): | 90 |
| Flow Rate (scfm): | 25 |
| Temperature (° F.): | Ambient |
| Relative Humidity (OEM specified): | <25% |
| Total Media Volume (ft³)/Mass (lbs) | |
| CS1: | 6.9 ft³/220 lbs |
| AC2: | 6.4 ft³/160 lbs |
| AC1: | 6.4 ft³/160 lbs |

The waste water treatment plant (WWTP) operated the carbon adsorption system on a monthly change out pattern. The unit is semi-continuous; therefore, uptime or skid hours were recorded at time of change out.

Figure 3:
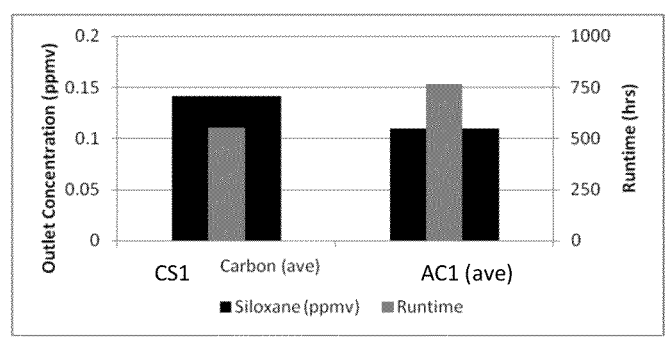
FIG. 3 shows a bar graph showing average values of siloxane levels (ppmv) and runtimes to breakthrough (hours) for averaged data collected for lignite-based activated carbon in a single (non-blended) type of media (AC1) and a media comprised of a blend of lignite-based activated carbon and a different carbon media (AC2) in comparison with a standard (non-lignite) coal activated carbon (CS1) according to an example of the present application.

As indicated, three activated carbon products were tested for siloxane removal capability. The 3 mm coal-based pellet (CS1) has been the standard media as specified by the original equipment manufacturer (OEM). Outlet gas samples were analyzed through gas chromatography-mass spectrometry (GC/MS) for all common siloxanes, as well as on total silicon (Si). On average, AC1 and AC2 products achieved 22% and 34%, respectively, less breakthrough on siloxanes and total Si than the standard media, respectively (FIG. 3). In addition, it was observed that AC1 and AC2 products logged 38% more runtime hours than the standard media. In this respect, the bar graph in FIG. 3 shows average values of siloxane levels (ppmv) and runtimes to breakthrough (hours) for averaged data collected for lignite-based activated carbon in a single (non-blended) type of media (AC1) and a media comprised of a blend of lignite-based activated carbon and a different carbon media (AC2) in comparison with a standard (non-lignite) coal activated carbon (CS1).

In a field test performed at Digester #1, the siloxane and other contaminant removal performance of AC1 was evaluated. Gas samples were taken from a 2-vessel (series configuration) carbon adsorption system using Summa canisters. A sampling assembly was used for diverting a small volume of the biogas, which included a tap line with a valve which could be opened to feed a gas sample into a Summa canister via a quick connect valve matching the tap line to the cannister. The gas sample collected in the Summa canister was analyzed to measure its contaminant contents. Samples were taken from the inlet and outlet. Analysis was performed on siloxane and VOC content via gas chromatography-mass spectrometry (GC/MS). $H_2S$ levels were also monitored using a Type L2 Oda-Log data logger. Sampling frequency for siloxanes and $H_{2S}$ was weekly and bi-weekly for VOC's. Analysis for siloxanes followed compendium method TO-15; analysis for VOC's followed TO-15+TIC. The standard operating conditions for the adsorption system are provided in FIG. 2. Change out frequency was modified to better evaluate performance. Determination of change out was dictated by the following criteria: siloxane breakthrough of a single siloxane species exceeds 150 ppbv in two consecutive sample periods, or a substantial spike in siloxane breakthrough is observed that may be critical to downstream equipment. The filter bed dimensions used in the field test were the same as indicated for the proof of concept study.

Although proof of concept was established, it is common for low but significant false positive values on D5 and D6 siloxanes to occur when using TEDLAR® bags. A silicone-based lubricant on the valve stem of TEDLAR® bag or in the sampling line may contribute a significant background level of siloxanes. Therefore, for the field tests, sampling was converted to Summa canisters to reduce this variability as well as to better support the increased frequency of testing.

As indicated, the field test experiment at Digester #1 provided findings for AC1. The emphasis of this test was to observe performance on siloxane removal. Therefore, in addition to monitoring siloxane concentration, $H_2S$ and VOC levels were monitored to evaluate competitive effects. $H_2S$ was observed to breakthrough first at 336 hours, followed by VOC breakthrough at 1098 hours, and lastly siloxanes (D4 only) at 2054 hours. The average inlet concentrations for all monitored biogas contaminants during this study are presented in Table 3.

TABLE 3

| Biogas Contaminants (ppmv) | | | | | | | |
|---|---|---|---|---|---|---|---|
| $H_2S$ | VOC (TO-15) | VOC (TO-15 + TIC) | L3 | L4 | D3 | D4 | D5 |
| 120 | 7 | 25 | 0.09 | 0.07 | 0.04 | 0.49 | 0.62 |

Figure 4:
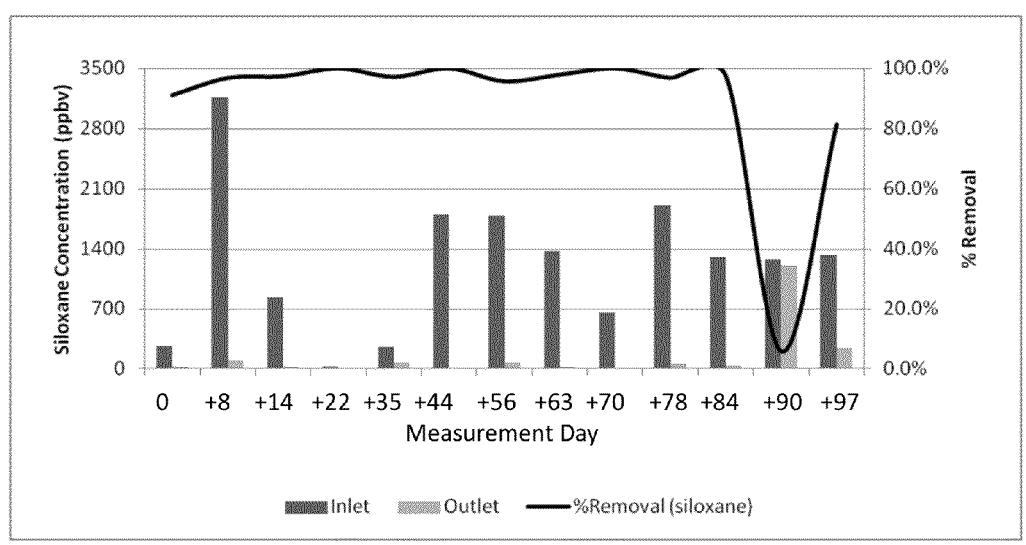
FIG. 4 shows a bar graph for a digester field test of the performance of lignite-based activated carbon in a single (non-blended) type of media (AC1) on siloxane removal (%) based on inlet and outlet measurements over a time period (days), and a curve for siloxane concentration (ppbv) over the test period, according to an example of the present application.

With respect to siloxane removal, the average siloxane concentration was 1.3 ppmv but has been as high as 3.2 ppmv. Complete removal of siloxanes was achieved with an average removal efficiency of 97.3% based on sample analysis, as shown in FIG. 4. Fluctuations in removal efficiency below 100% are attributed to values considered below GC/MS detection limits and the "L2 phenomena" (Wheless, E. et al., Siloxanes in landfill and digester gas update. In *Proc. 27th SWANA Landfill Gas Symp.*, San Antonio, Tex., March 22-25; Solid Waste Assoc. North America Silver Springs, Md.; 2004). The "L2 Phenomena" is the appearance of L2 in the outlet stream when it is not present in or greatly exceeds the inlet stream. There was no detection of L2 at the inlet for the duration of this test but L2 would appear randomly between 10 and 60 ppbv at the outlet.

AC1 was in operation for 2054 hours before the observation of breakthrough. According to the OEM, this greatly exceeds the longest observed media life for their traditional media (CS1, 60 CTC), which was 952 hours. At 2054 hours, siloxane D4 showed complete breakthrough and siloxane L3 showed minimal breakthrough. However, a check sample was taken to confirm breakthrough; the check sample showed 20% D4 breakthrough with all other siloxanes remaining non-detect or below GC/MS detection limits. Given that the breakthrough value exceeded 150 ppbv for two consecutive samples, the media was changed out to protect the downstream microturbine.

Based on time-to-breakthrough, a total siloxane loading between 2.1% and 2.3% by weight is estimated. Based on consolidated testing summaries by Ajhar, M. et al., *Bioresource Techn.*, 101 (2010), 2913-2923, this loading capacity greatly exceeds the typical loading capacities for traditional activated carbons and rivals silica gel as observed in historical field testing (see Table 4 below). The historical operating pattern for this digester was 600-960 hours using non-lignite coal-based activated carbon. That pattern translates to 0.57-0.91% siloxane loading on carbon by weight, which correlates well with Table 4. Table 5 presents the estimated loading for measured siloxanes at the time of D4 initial breakthrough when using AC1. The data collection for the field test was stopped at the initial breakthrough of D4. The values presented here are understated since carbon was not taken to full breakthrough or saturation. L3, L4, D3, and D5 did not breakthrough before the initial breakthrough of D4. The time to breakthrough for the other siloxane species would have been on an order of at least over about 50% greater, or about 100% greater than for D4.

TABLE 4

| | Media Type | | | |
|---|---|---|---|---|
| | Coconut AC | Graphite AC | Silica Gel | General AC |
| Performances (% by wt) | 0.4-1.0 | 0.6-1.5 | 1.0-2.2 | 0.2-1.5 |

TABLE 5

| | Siloxane: | | | | |
|---|---|---|---|---|---|
| | L3 | L4 | D3 | D4 | D5 |
| Loading Capacity (% by wt.): | >0.6 | >0.6 | >1.4 | >2.7 | >3.2 |

With respect to general observations on $H_2S$/VOC removal and competitive effects, AC1 was evaluated for preferential adsorption to siloxanes while minimizing the competitive effects of VOC's and total reduced sulfur compounds. $H_2S$ breakthrough occurred after approximately 336 hours, achieving approximately 3.3% loading by weight. $H_2S$ is not physically loaded onto activated carbon. It is chemically and catalytically converted by various reaction pathways. AC1 has been tested to demonstrate a high alkalinity and high catalytic activity (2.26 meq/g neutralizing capacity).

VOC breakthrough occurred in 1098 hours suggesting an overall loading capacity of 5.3% by weight. VOC content was a mixture of alkanes, ketones, and aromatics. An interesting finding was continued complete removal of ketones and aromatics (BTEX) even after complete breakthrough of all other VOC's was observed. Benzene and toluene breakthrough occurred between 1500 and 1700 hours although xylene removal remained at 100% at time of change out. Ultimately, given the observed loading capacities, siloxane breakthrough would have been 216 hours (if sulfur-driven), 600 hours (if VOC-driven), or 1008 hours (if BTEX-driven). Siloxane breakthrough occurred in 2054 hours suggesting greatly reduced competitive effects when using AC1.

The results of the Digester #1 field tests show that the AC1 and AC2 products have high siloxane removal capacity with minimal competitive influences from other contaminants. AC1, for example, demonstrated a 215% improvement in bed life at the digester.

Example 2

In a field test conducted at Digester #2, AC2 was installed in the primary vessel of a lead/lag system. When tested, CS2 (4 mm pellets; 60 CTC activity) were installed in the secondary vessel. Gas samples were taken via TEDLAR® bag at the inlet and outlet to measure siloxane concentration.

AC2 was investigated for siloxane removal performance at a digester site that historically used the segmented activity gradient (SAG) or layered bed methodology. Prior to testing AC2, a baseline was established using 4 mm activated carbon pellets with 60 CTC activity (CS2). Once removal efficiency was established, AC2 was installed in the primary vessel with CS2 remaining in the secondary vessel. The filter bed dimensions used were 275 cm depth and 183 cm diameter. This was a 3-vessel lead-lag system with two vessels operating and a third on standby. All vessels had the same dimensions and bed depth. Five historical data points for SAG media, one data point for CS2, and five data points for the AC2 combination were evaluated. The five data points for SAG performance was collected approximately once a month over four consecutive months. The AC2 data was collected approximately once a month over five consecutive months. The CS2 data point was collected approximately one month after the last data point was collected for SAG and one month before the first data point was collected for AC2.

Table 5 presents the results for siloxane removal performance of the tested media. Inlet and outlet siloxane concentrations (ppm) measured before and after flowing through the media are indicated from which the % Removal was calculated.

TABLE 5

| Data Point | Inlet | Outlet | % Removal |
|---|---|---|---|
| | SAG | | |
| 1 | 0.63 | 0.09 | 86% |
| 2 | 1.1 | 0.04 | 96% |
| 3 | 2.3 | 0.1 | 96% |
| 4 | 0.31 | 0.08 | 74% |
| | CS2 | | |
| 1 | 0.2 | 0.02 | 90% |
| | AC2 | | |
| 1 | 3.9 | 0.05 | 99% |
| 2 | 0.68 | 0.14 | 79% |
| 3 | 1.6 | 0.04 | 98% |
| 4 | 2.8 | 0.04 | 99% |
| 5 | 1.9 | 0.03 | 98% |

On average, the addition of AC2 enhanced siloxane removal. The average removal efficiency for SAG was 93% whereas the introduction of AC2 improved performance to 97%. Variability on the outlet was also reduced. AC2 controlled outlet concentrations of siloxanes to a variability of ±85 ppb; SAG media variability was ±253 ppb. Although not desiring to be bound to any theory, it is theorized that AC2 offers greater homogeneity for the entire vessel volume compared to layering. During the AC2 trial, engine oil life was observed to be increased by a factor of three. In addition, it was noted that spark plugs were noticeably "cleaner" or residue-free. Both of these are indicative of improved siloxane removal. Specifically, a 200% increase in engine oil life from 1,000 hours to 3,000 hours, and greater than 25% increase in spark plug life, and improved siloxane removal efficiency were observed.

The results of the Digester #2 field tests show that the AC2 product has high siloxane removal capacity with minimal competitive influences from other contaminants.

Example 3

In field tests performed at Landfill #1, AC2 was installed in a two-vessel lead/lag system. The filter bed dimensions used were 152 cm depth and 275 cm diameter. Samples were taken from the inlet, in-between, and outlet locations via TEDLAR® bag. Analysis was performed on siloxane, total reduced sulfur (TRS), and VOC content via GC/MS. Sampling frequency was weekly. AC2 was evaluated as an alternative to SAG methodology. A lead/lag system was utilized where the vessel change outs occur approximately every 12 days. After 12 days, the secondary vessel is switched to primary position, the primary vessel is then changed out with fresh media, and placed in the secondary position. At time of change out, both TRS and siloxane species were trending at 100% removal; VOC removal was 92% at change out. The plant was shut down at 20 days into the field test for reasons unrelated to the field test. 20 days of at least 99% siloxane removal was observed prior to the shutdown (inlet concentration=4-8 ppm), 100% sulfur removal (TRS) (inlet concentration=100-160 ppm), and approximately at least 95% VOC removal (inlet concentration=25-100 ppm). Gas analysis showed 100% removal of both siloxanes and TRS at the time of plant shut down. Based on the results observed up until shutdown, the bed life forecast was 30-35 days as an estimate based on breakthrough on the lead vessel, and the lag vessel showed 0% breakthrough.

Figure 5:
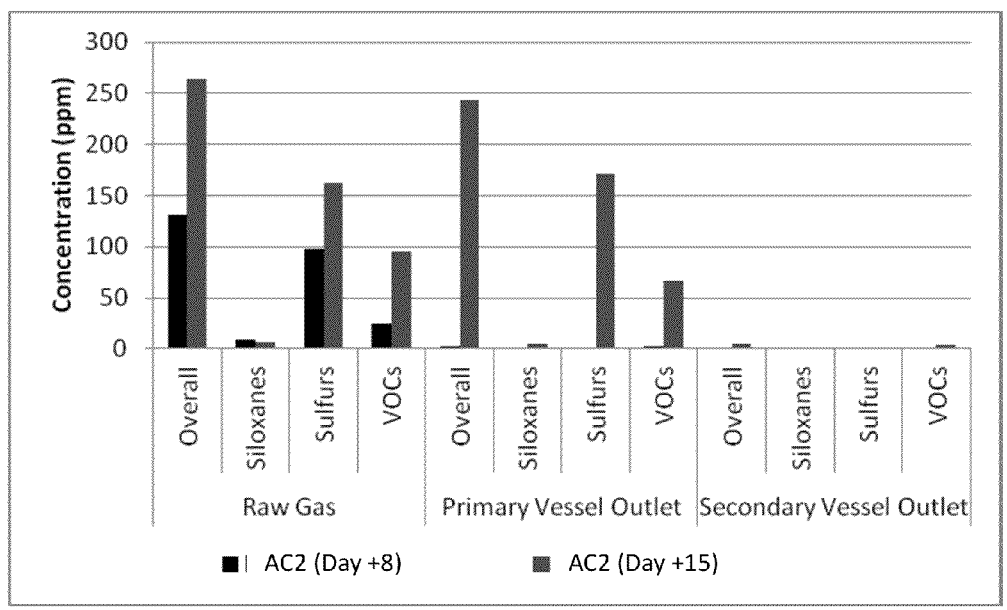
FIG. 5 shows a bar graph of gas analysis for a landfill test of the removal performance of a media comprised of a blend of lignite-based activated carbon and a different carbon media (AC2) at two different dates with contaminant concentrations (ppm) for siloxanes, sulfurs, VOCs and overall shown for raw gas, a primary vessel outlet, and a secondary vessel outlet, according to an example of the present application.

Breakthrough had been observed at the outlet of the primary vessel; essentially, $H_2S$ had completely broken through with VOC's and siloxanes showing initial signs of breakthrough, as shown in FIG. 5.

Figure 6:
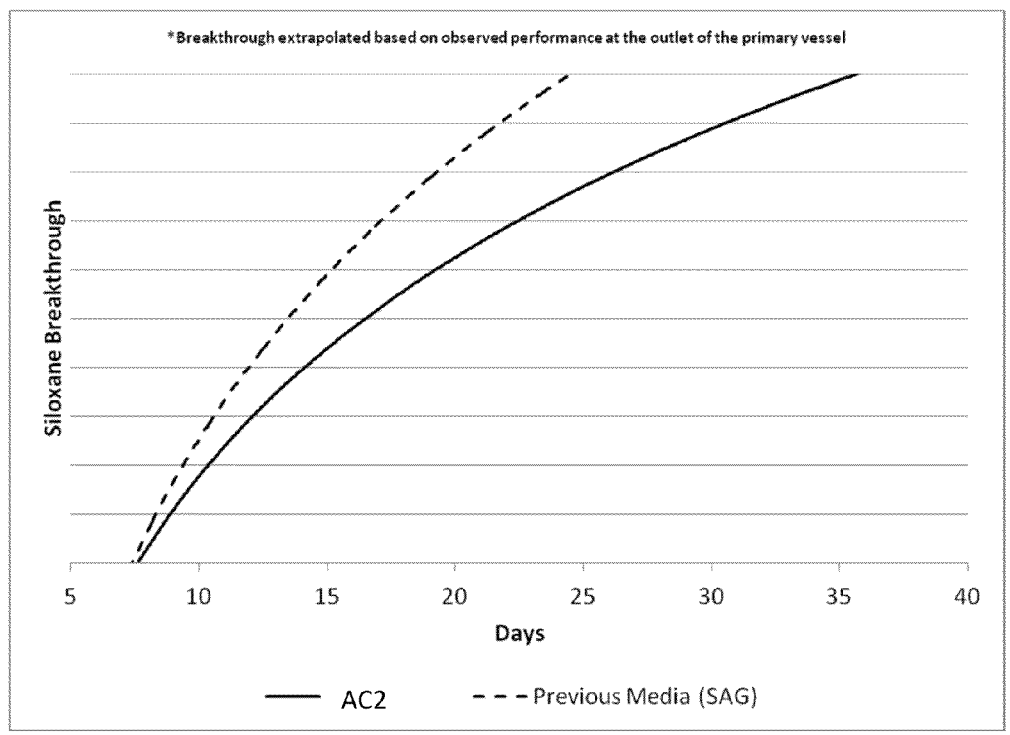
FIG. 6 shows extrapolated breakthrough curves with respect to the number of days to breakthrough for a previous layered bed media blend in comparison to a media comprised of a blend of lignite-based activated carbon and a different carbon media (AC2) according to an example of the present application.

There were insufficient historical records to make a comparative assessment to previous media. However, the performance observed in the field test indicates that AC2 is a viable alternative to the SAG methodology. Extrapolation of primary vessel breakthrough data indicates a potential 30% improvement in media longevity and performance compared to the normal operating pattern, such as shown in FIG. 6.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferable range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of removing siloxanes from a contaminated gas stream, comprising flowing the gas stream comprising siloxanes through an adsorbent media to remove at least part of the siloxanes from the gas stream, wherein said adsorbent media comprises lignite-based activated carbon having an apparent density of from about 0.3 to about 0.6 g/mL.

2. The method of claim 1, wherein the lignite-based activated carbon has pore sizes and a total pore volume, wherein at least about 25% of the total pore volume is from pore sizes of from 20 Å to 500 Å.

3. The method of claim 1, wherein the siloxanes comprise linear siloxanes, cyclic siloxanes, or any combinations thereof.

4. The method of claim 1, wherein the siloxanes comprise polymethylpolysiloxane, polymethylcyclopolysiloxane, or any combinations thereof.

5. The method of claim 1, wherein the lignite-based activated carbon has a molasses decolorizing efficiency of at least 50.

6. The method of claim 1, wherein the flowing of the gas through the adsorbent media removes at least about 95 wt. % of the volatile siloxanes for a time period that is at least about 3× longer than for adsorbent media containing an equal volume and same bed geometry of bituminous coal-based activated carbon instead of the lignite-based activated carbon.

7. The method of claim 1, wherein the lignite-based activated carbon has a total porosity of from about 0.9 to about 2.0 mL/g.

8. The method of claim 1, wherein the lignite-based activated carbon has a BET surface area of from about 500 to about 650 $m^2/g$.

9. The method of claim 1, wherein the lignite-based activated carbon has a pH greater than 7.

10. The method of claim 1, wherein the lignite-based activated carbon is in powder form or bound form.

11. The method of claim 1, wherein the lignite-based activated carbon is in the form of granular particles, briquettes, or extruded pellets.

12. The method of claim 1, wherein the adsorbent media comprises a blend of the lignite-based activated carbon and silica gel.

13. The method of claim 1 wherein the lignite-based activated carbon is steam-activated unwashed lignite.

14. The method of claim 1, wherein the adsorbent media comprises at least about 50 wt. % lignite-based activated carbon.

15. The method of claim 1, wherein the adsorbent media comprises a blend of the lignite-based activated carbon and at least one non-carbon based adsorbent media.

16. The method of claim 1, wherein the adsorbent media is present as a homogenous bed of the lignite-based activated carbon.

17. The method of claim 1, wherein the adsorbent media comprises a blend of the lignite-based activated carbon and at least one different kind of adsorbent media.

18. The method of claim 17, wherein the adsorbent media comprises a blend of the lignite-based activated carbon and at least one different kind of activated carbon, and wherein at least one of the lignite-based activated carbon and the at least one different kind of activated carbon are impregnated with at least one impregnant that is a salt, an acid, or base.

19. The method of claim 1, wherein the adsorbent media comprises a blend of the lignite-based activated carbon and at least one different kind of activated carbon.

20. The method of claim 19, wherein the at least one different kind of activated carbon is activated carbon produced from bituminous coal, coconut shells, wood, sawdust, rice hulls, peat, petroleum residues, or any combinations thereof.

21. The method of claim 19, wherein the at least one different kind of activated carbon has a pore size distribution comprising a percentage of pores having pore sizes less than 2 nm that is greater than a percentage of pores in the lignite-based activated carbon that has pore sizes less than 2 nm.

22. The method of claim 1, wherein the gas stream comprises landfill gas emissions.

23. The method of claim 1, wherein the gas stream comprises gas emissions from anaerobic digestion.

24. The method of claim 1, wherein the flowing of the gas stream through the adsorbent media removes at least about 95 wt. % of the volatile siloxanes from the gas stream.

25. The method of claim 1, wherein the flowing of the gas through the adsorbent media removes at least about 95 wt. % of the volatile siloxanes for a time period that is at least about 2× longer than for adsorbent media containing an equal volume and same bed geometry of bituminous coal-based activated carbon instead of the lignite-based activated carbon.

26. The method of claim 1, wherein the gas stream at the inlet side of the adsorbent media contains from about 1 ppm to about 25 ppm siloxane.

27. The method of claim 1, wherein the gas stream comprises volatile siloxanes, total reduced sulfur compounds and volatile organic compounds, when introduced at an inlet side of the adsorbent media.

28. The method of claim 27, wherein the flowing of the gas stream through the adsorbent media removes at least about 95 wt. % of the volatile siloxanes from the gas stream.

29. The method of claim 27, wherein the flowing of the gas stream through the adsorbent media removes at least about 95 wt. % of total reduced sulfur compounds.

30. The method of claim 27, wherein the flowing of the gas stream through the adsorbent media removes at least about 90 wt. % of the volatile organic compounds from the gas stream.

31. The method of claim 27, wherein the flowing of the gas stream through the adsorbent media removes at least about 99 wt. % of the volatile siloxanes from the gas stream.

32. The method of claim 27, wherein the flowing of the gas stream through the adsorbent media removes at least about 99 wt. % of the volatile siloxanes, and at least one of i) at least about 99.5 wt. % of the total reduced sulfur compounds and ii) at least about 95 wt. % of the volatile organic compounds from the gas stream.

33. The method of claim 27, wherein the flowing of the gas through the adsorbent media removes at least about 95 wt. % of the volatile siloxanes for a time period that is at least about 2× longer than for adsorbent media containing an equal volume and same bed geometry of bituminous coal-based activated carbon instead of the lignite-based activated carbon.

34. The method of claim 27, wherein the flowing of the gas through the adsorbent media removes at least about 95 wt. % of the volatile siloxanes for a time period that is at least about 3× longer than for adsorbent media containing an equal volume and same bed geometry of bituminous coal-based activated carbon instead of the lignite-based activated carbon.

35. The method of claim 27, wherein the gas stream at the inlet side of the adsorbent media contains from about 1 ppm to about 25 ppm siloxanes, from about 10 ppm to about 150 ppm total reduce sulfur compounds, and from about 200 ppm to about 500 ppm volatile organic compounds.

36. A method of removing siloxanes from a contaminated gas stream, comprising flowing the gas stream comprising siloxanes through an adsorbent media to remove at least part of the siloxanes from the gas stream, wherein said adsorbent media comprises lignite-based activated carbon having a total porosity of from about 0.9 to about 2.0 mL/g.

37. The method of claim 36, wherein the lignite-based activated carbon has pore sizes and a total pore volume, wherein at least about 25% of the total pore volume is from pore sizes of from 20 Å to 500 Å.

38. The method of claim 36, wherein the lignite-based activated carbon has a molasses decolorizing efficiency of at least 50.

39. The method of claim 36, wherein the lignite-based activated carbon has a total porosity of from about 0.9 to about 2.0 mL/g.

40. The method of claim 36, wherein the lignite-based activated carbon has a BET surface area of from about 500 to about 650 m²/g.

41. The method of claim 36, wherein the lignite-based activated carbon has a pH greater than 7.

42. The method of claim 36, wherein the lignite-based activated carbon is in powder form or bound form.

43. The method of claim 36, wherein the lignite-based activated carbon is in the form of granular particles, briquettes, or extruded pellets.

44. The method of claim 36, wherein the lignite-based activated carbon is steam-activated unwashed lignite.

45. The method of claim 36, wherein the adsorbent media comprises at least about 50 wt. % lignite-based activated carbon.

46. The method of claim 36, wherein the adsorbent media is present as a homogenous bed of the lignite-based activated carbon.

47. The method of claim 36, wherein the adsorbent media comprises a blend of the lignite-based activated carbon and at least one different kind of adsorbent media.

48. The method of claim 47, wherein the adsorbent media comprises a blend of the lignite-based activated carbon and at least one different kind of activated carbon, and wherein at least one of the lignite-based activated carbon and the at least one different kind of activated carbon are impregnated with at least one impregnant that is a salt, an acid, or base.

49. The method of claim 36, wherein the flowing of the gas stream through the adsorbent media removes at least about 95 wt. % of the volatile siloxanes from the gas stream.

50. The method of claim 36, wherein the flowing of the gas through the adsorbent media removes at least about 95 wt. % of the volatile siloxanes for a time period that is at least about 2× longer than for adsorbent media containing an equal volume and same bed geometry of bituminous coal-based activated carbon instead of the lignite-based activated carbon.

51. The method of claim 36, wherein the gas stream at the inlet side of the adsorbent media contains from about 1 ppm to about 25 ppm siloxanes.

52. The method of claim 36, wherein the gas stream comprises volatile siloxanes, total reduced sulfur compounds and volatile organic compounds, when introduced at an inlet side of the adsorbent media.

53. The method of claim 36, wherein the gas stream comprises landfill gas emissions.

54. The method of claim 36, wherein the gas stream comprises gas emissions from anaerobic digestion.

55. An adsorbent media comprising lignite-based activated carbon and having siloxanes adsorbed or attached therein, wherein the lignite-based activated carbon has a pore size distribution of:
about 20% to about 36% of total pore volume from pore sizes less than 20 Å,
about 25% to about 40% of total pore volume from pore sizes of from 20 Å to 500 Å, and
about 40% to about 44% of total pore volume from pore sizes greater than 500 Å.

* * * * *